United States Patent [19]

Pyles

[11] Patent Number: 5,669,882
[45] Date of Patent: Sep. 23, 1997

[54] CURVED EPIDURAL NEEDLE SYSTEM

[76] Inventor: Stephen Pyles, P.O. Box 1626, Ocala, Fla. 34478

[21] Appl. No.: 636,855

[22] Filed: Apr. 23, 1996

[51] Int. Cl.$^6$ ..................................................... A01M 5/178
[52] U.S. Cl. ................... 604/164; 604/44; 604/158; 604/264; 128/772
[58] Field of Search .................. 604/44, 158, 164, 604/264; 128/772

[56] References Cited

U.S. PATENT DOCUMENTS

| | | | |
|---|---|---|---|
| 2,922,420 | 1/1960 | Cheng | 604/158 |
| 4,721,506 | 1/1988 | Teves | 604/164 X |
| 4,976,691 | 12/1990 | Sahota | 128/772 X |
| 4,994,036 | 2/1991 | Biscoping et al. | 604/164 X |
| 5,279,570 | 1/1994 | Dombrowski et al. | 604/164 |

*Primary Examiner*—Sam Rimell
*Assistant Examiner*—Robert V. Racunas

[57] ABSTRACT

A needle and stylus system. The system has a hollow tubular needle formed of a rigid material. The needle has an elongated linear intermediate section constituting the majority of the length of the needle and with a curved distal section terminating in an oval opening. A bore is formed through the intermediate and distal sections of an essentially common diameter and the oval opening at the distal end is located in a plane essentially parallel with the axis of the intermediate section and spaced from the exterior surface of the intermediate section. The needle also has a proximal end formed as a radially exterior enlargement with an enlarged cylindrical bore. A tubular stylet has an elongated linear intermediate section and a curved distal section with an oval planar face positionable at the opening at the distal end of the needle when the stylet is inserted within the needle. The style also has a semi-cylindrical section between the intermediate section and the distal section to allow the bending thereof as the styler is moved into the needle with its distal section approaching the distal section of the needle. The stylet has a proximal end with an exterior radial enlargement to be grasped by an operator and an intermediate radial enlargement receivable within the enlarged cylindrical bore at the proximal end of the needle.

2 Claims, 2 Drawing Sheets

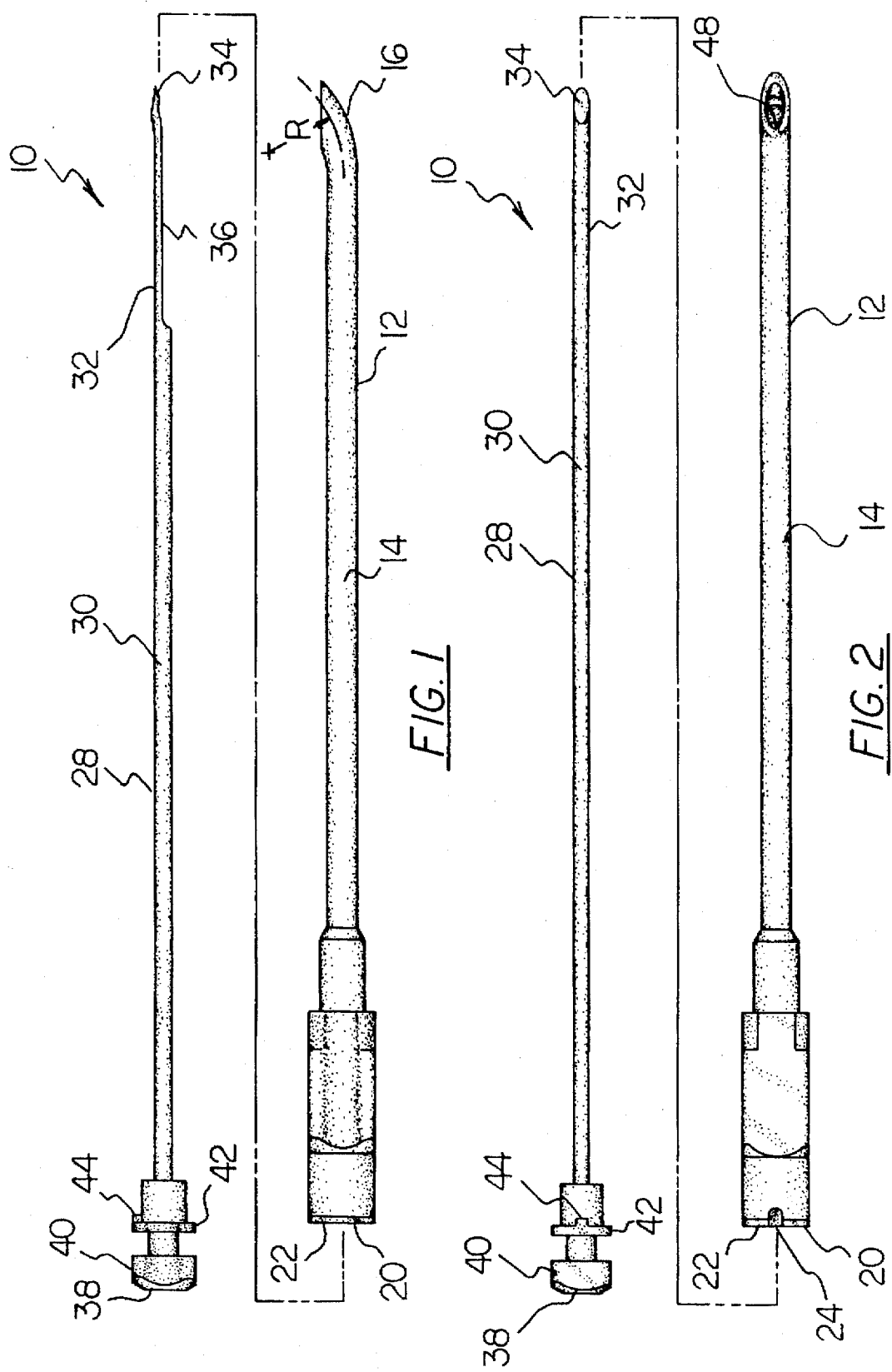

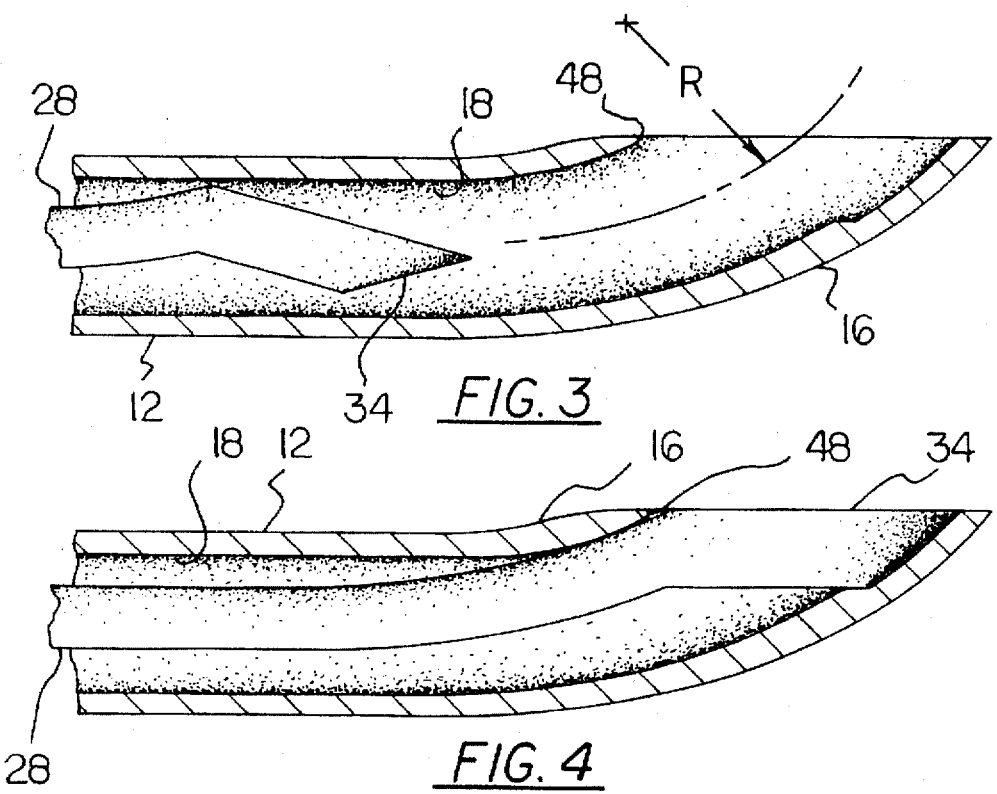
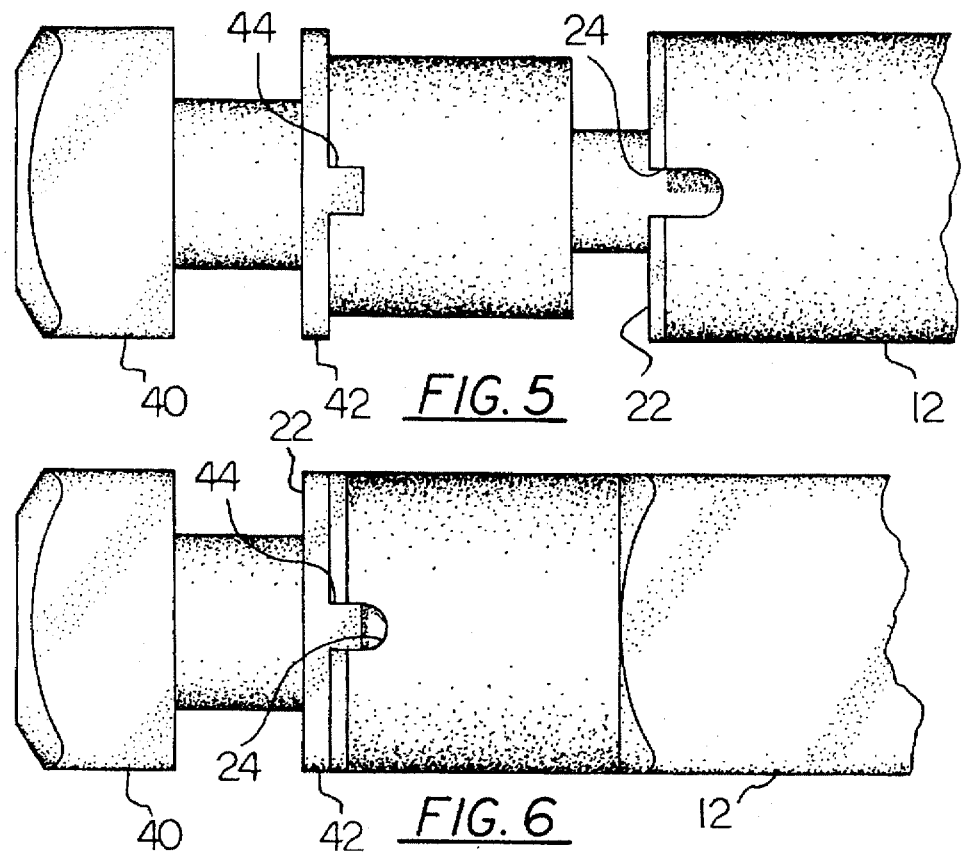

5,669,882

CURVED EPIDURAL NEEDLE SYSTEM

BACKGROUND OF THE INVENTION

1. Field of the Invention

The present invention relates to a curved epidural needle system and more particularly pertains to placement of epidural electrodes for a procedure known as spinal cord stimulation with a curved epidural needle system.

2. Description of the Prior Art

The use of needles, stylets and other associated components and systems of various designs and configurations is known in the prior art. More specifically, needles, stylets and other associated components and systems of various designs and configurations heretofore devised and utilized for the purpose of injecting or placing materials into a patient through various methods and apparatuses are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,349,023 to Gross discloses a device which will permit the introduction of a length of catheter tubing through a needle and into the epidural space of a patient wherein the chance of the tubing being kinked is substantially reduced. In one version, an adapter having two opposing protruding sections is provided with one protrusion fitting inside the hub cavity of an epidural needle and the other extending outwardly to provide a finger engaging orifice surface. With one of the protruding sections placed in the needle hub cavity a continuous passageway is provided from the outwardly protruding section having the finger engaging surface and through the passageway of the adapter which will be aligned with the passageway in the epidural needle ultimately communicating with the needle. In an alternative embodiment, the protruding section extends from the hub of an epidural needle and a continuous passageway is provided therethrough to the needle as well as the protrusion providing a finger engaging surface so that the small diameter tubing can be easily fed therein.

U.S. Pat. No. 4,518,383 to Evans discloses an instrument for epidural and spinal anaesthesia which has outer and inner needle assemblies. The outer assembly has a hollow needle, the forward end of which is bent at an angle of about 20 degrees and has an inclined, pointed tip that makes an angle of about 10 degrees with the axis of the instrument. The needle has a hub at its rear end which is provided with a keyway on its outer surface. The inner assembly has a hollow needle that extends within the needle of the outer assembly and projects from its forward end. The inner needle also has an inclined, pointed tip that makes an angle of about 30 degrees with the axis of the instrument. The tips of the two needles lie in plans substantially at right angles to each other. At its rear end, the inner assembly has a transparent hub with a key that locates in the keyway so as to ensure correct orientation of the two assemblies.

U.S. Pat. No. 4,889,529 to Haindl discloses a needle. One side wall of a rigid needle tub is provided at its front end with a curved bending directed toward the opposite, axial-side wall and has a lumen opening formed therein. The lumen opening is provided with a rear inner cutting edge and a front punctuating portion which comprises a lancet-shaped tip having a facet grinding. The tip is arranged in a zone defined by two imaginary lines extending respectively from the inner surface and the outer surface of the axial side wall beyond the rear cutting edge of the lumen opening. When using the needle, no material is punched out of the material to be perforated.

Lastly, U.S. Pat. No. 4,958,901 to Coombs, discloses a method for producing a multi-lumen needle suitable for administrating spinal anesthesia. The method will provide a needle that will allow the simultaneous administration of spinal and epidural anesthetic from a single site. A preferred needle made by this method can optionally be made with a stock configuration which has means for holding a catheter during the insertion of a spinal needle and is configured so as to provide gripping sites to assist in positioning the needle. The preferred needle has a lumen which can serve as a spinal introducer. The introducer lumen sheaths the spinal needle until the spinal needle is in the epidural space. This assures that the spinal needle will not be bent or fractured in use by impingement with bone or hard tissue.

While these devices fulfill their respective, particular objective and requirements, the aforementioned patents do not describe a curved epidural needle system for placement of epidural electrodes for a procedure known as spinal cord stimulation.

In this respect, the curved epidural needle system according to the present invention substantially departs from the conventional concepts and designs of the prior art, and in doing so provides an apparatus primarily developed for the purpose of placement of epidural electrodes for a procedure known as spinal cord stimulation.

Therefore, it can be appreciated that there exists a continuing need for new and improved curved epidural needle system which can be used for placement of epidural electrodes for a procedure known as spinal cord stimulation. In this regard, the present invention substantially fulfills this need.

Measurements of Needle and Stylet:
needle: 10.5 cm
intermediate section: 8.1 cm
curved distal end: 0.8 cm
internal diameter: between 0.066 cm and 0.0685 cm
outer diameter: between 0.082 cm and 0.084 cm
stylet: 11.1 cm
intermediate section: 8.1 cm
semi-cylindrical section: 2.1 cm

BRIEF DESCRIPTION OF THE DRAWINGS

For a fuller understanding of the nature and objects of the invention, reference should be had to the following detailed description taken in connection with the accompanying drawings in which:

FIG. 1 is a exploded side elevational view of the new and improved needle used for the placement of epidural electrodes constructed in accordance with the principles of the present invention.

FIG. 2 is a view similar to FIG. 1 but with the needle and stylet rotated 90 degrees.

FIGS. 3 and 4 illustrate the movement of the distal end of the stylet as it moves to the distal end of the needle.

FIGS. 5 and 6 illustrate the coupling of the proximal ends of the needle in their proper aligned orientation.

Similar reference characters refer to similar parts throughout the several Figures.

DESCRIPTION OF THE PREFERRED EMBODIMENT

With reference now to the drawings, and in particular to FIG. 1 thereof, a new and improved needle used for the placement of epidural electrodes embodying the principles and concepts of the present invention and generally designated by the reference numeral 10 will be described.

The present invention, the new and improved needle used for the placement of epidural electrodes for a procedure known as spinal cord stimulation, is comprised of a plurality of components. Such components in their broadest context simply include a needle and a stylus. Such components are individually configured and correlated with respect to each other so as to attain the desired objective.

The present invention is a system 10. The system is comprised of a needle 12. Such needle is used for the placement of epidural electrodes for a procedure known as spinal cord stimulation. The needle is a hollow tubular needle about 10.5 centimeters, plus or minus 10 percent, in length and is formed of a rigid material. The needle also has an elongated linear intermediate section 14. Such section is about 8.1 centimeters, plus or minus 10 percent, in length and thereby constitutes the majority of the length of the needle. The needle also has a curved distal section 16 about 0.8 centimeters, plus or minus 10 percent, in length. Such distal end has a radius of curvature or between about 2 and 4 centimeters which terminates in an oval opening. The outer diameter is between about 0.082 and 0.084 centimeters.

A small bore 18 is formed through the entire intermediate and distal sections. Such bore is of an essentially common internal diameter between about 0.066 and 0.0685 centimeters. The bore has an oval opening at the distal end which is located in a plane essentially parallel with the axis of the intermediate section. The plane of the distal bore is spaced from the exterior surface of the intermediate section. The needle also has a proximal end 20 formed as a radially exterior enlargement with an enlarged cylindrical bore 22 and an alignment slot 24 at the proximal end of the enlargement.

The system 10 of the present invention further includes a tubular stylet 28. The stylet is about 11.1 centimeters, plus or minus 10 percent, in length. The stylet has an elongated linear intermediate section 30. Such intermediate section is about 8.1 centimeters, plus or minus 10 percent, in length. The intermediate section has a curvable distal section 32 with an oval planar face 34. Such planar face is positionable at the opening at the distal end of the needle when the stylet is fully inserted within the needle.

The stylet also has a semi-cylindrical section 36 about 2.1 centimeters, plus or minus 10 percent, in length. Such section is located between the intermediate section and the distal end. This allows the bending of the semi-cylindrical section to conform with the needle as the stylet is moved into the needle with its distal section approaching the distal section of the needle.

The stylet has a proximal end 38 with an exterior radial enlargement 40 for being grasped by an operator. The stylet also has an intermediate radial enlargement 42 which is receivable within the enlarged cylindrical bore at the proximal end of the needle. Also included is a distally extending alignment projection 44 positionable in the alignment slot. Such arrangement functions to ensure alignment of the planar face of the stylet into the distal opening of the needle.

As can be seen in the various Figures, the size of the needle and stylet are such that the intermediate section of the needle constitutes between 75 and 85 percent, preferably about 80 percent of the length of the entire needle. Similarly, the intermediate section of the stylet constitutes between about 68 and 78 percent, preferably about 73 percent of the length of the entire stylet.

As can be seen in FIGS. 1 and 2, as well as in the enlarged showing of FIGS. 3 and 4, the needle at its distal end has an interior orifice 48 with a configuration which is smooth and essentially rounded and which is enlarged as compared to prior art needle openings. Such configuration allows for the advancement and with withdrawal of electrodes as well as for the rotation of the needle during use with a decreased chance of sheering an electrode or of cutting a patient. Further, as can be seen in the figures, the distal opening includes an upturned bevel which improves directional control by a physician during rotation of the needle.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed as being new and desired to be protected by Letters Patent of the United States is as follows:

1. A needle and stylus system comprising:

a hollow tubular needle formed of a rigid material having an elongated linear intermediate section constituting the majority of the length of the needle and with a curved distal section terminating in an oval opening, the oval opening having an upturned bevel which improves directional control by a physician during rotation of the needle, a bore formed through the intermediate and distal section of an essentially common diameter and with the oval opening at the distal section located in a plane essentially parallel with an axis of the intermediate section and spaced from an exterior surface of the intermediate Section, the needle also having a proximal end formed as a radially exterior enlargement with an enlarged cylindrical bore; and a tubular stylet having an elongated linear intermediate section and with a curved distal section with an oval planar face positionable at the opening at the distal end of the needle when the style is inserted within the needle, the stylet also having a semi-cylindrical section between the intermediate section and the distal section to allow the bending thereof as the stylet is moved into the needle with its distal section approaching the distal section of the needle, the stylet having a proximal end With an exterior radial enlargement for being grasped by an operator and an intermediate radial enlargement receivable within the enlarged cylindrical bore at the proximal end of the needle.

2. A new and improved needle used for the placement of epidural electrodes for a procedure known as spinal cord stimulation comprising, in combination:

a hollow tubular needle about 10.5 centimeters in length formed of a rigid material having an elongated linear intermediate section about 8.1 centimeters in length constituting the majority of the length of the needle and with a curved distal section about 0.8 centimeters in length and radius of curvature of between 2 and 4 centimeters and terminating in an oval opening, the oval opening having an upturned bevel which improves directional control by a physician during rotation of the needle, a small bore formed through the entire intermediate and distal section of an essentially common internal diameter of between about 0.0660 and 0.0685 centimeters and with the oval opening at the distal section located in a plane essentially parallel with an axis of the intermediate section and spaced from an exterior surface of the intermediate section, the needle also having a proximal end formed as a radially exterior enlargement with an enlarged cylindrical bore and an alignment slot at a proximal end of the enlargement; and a tubular stylet about 11.1 centimeters in length having an elongated linear intermediate section about 8.1 centimeters in length and with a curved distal section with an oval planar face positionable at the opening at the distal section of the needle when the stylet is fully inserted within the needle, the stylet also having a semi-cylindrical section about 2.1 centimeters in length between the intermediate section and the distal end to allow the bending thereof as the stylet is moved into the needle with its distal section approaching the distal section of the needle, the stylet having a proximal end with an exterior radial enlargement for being grasped by an operator and an intermediate radial enlargement receivable within the enlarged cylindrical bore at the proximal end of the needle and with a distally extending alignment projection positionable in the alignment slot to ensure alignment of the planar face of the stylet into the distal opening of the needle.

* * * * *